United States Patent [19]

Newman

[11] Patent Number: 4,931,046

[45] Date of Patent: Jun. 5, 1990

[54] IONTOPHORESIS DRUG DELIVERY SYSTEM

[76] Inventor: Martin H. Newman, 77 Norwood St., Sharon, Mass. 02067

[21] Appl. No.: 314,297

[22] Filed: Feb. 22, 1989

Related U.S. Application Data

[63] Continuation of Ser. No. 51,079, May 15, 1987, abandoned.

[51] Int. Cl.$^5$ ............................................. A61N 1/30
[52] U.S. Cl. .................................. 604/20; 128/419 R; 128/80 B
[58] Field of Search .................. 604/20; 128/798, 802, 128/803, 419 R

[56] References Cited

U.S. PATENT DOCUMENTS

| | | |
|---|---|---|
| 3,163,166 | 12/1964 | Brant et al. |
| 4,141,359 | 2/1979 | Jacobsen et al. ........................ 604/20 |
| 4,702,732 | 10/1987 | Powers et al. ........................ 604/20 |
| 4,708,716 | 11/1987 | Sibalis ................................... 604/20 |

FOREIGN PATENT DOCUMENTS

| | | | |
|---|---|---|---|
| 0092015 | 10/1983 | European Pat. Off. ............... | 604/20 |
| 2260359 | 9/1975 | France ................................... | 604/20 |
| 2500689 | 8/1982 | France ................................... | 604/20 |
| 2064178 | 6/1981 | United Kingdom ................... | 604/20 |
| 8607269 | 12/1986 | World Int. Prop. O. ............ | 604/20 |

OTHER PUBLICATIONS

Spencer, "Programmable . . . Iontophoresis", Med & Biol. Eng., vol. 9, pp. 683–702, 1971.

*Primary Examiner*—Lee S. Cohen
*Attorney, Agent, or Firm*—Robert F. O'Connell

[57] ABSTRACT

A transdermal medication delivery system in which the medication is retained in a non-charged form such that it can be electrically charged. A d-c electrical current is supplied through the retained medication when it is in its electrically charged form and current control is used to control the current level. The electrical current supply circuit, the control circuit, the retained charged medication, and the body location of a patient to which the medication is to be delivered transdermally, form a closed loop during operation so that the current is maintained at a substantially constant level while being delivered to the body location. Such delivery can be terminated if the current exceeds a maximum allowable level.

18 Claims, 3 Drawing Sheets

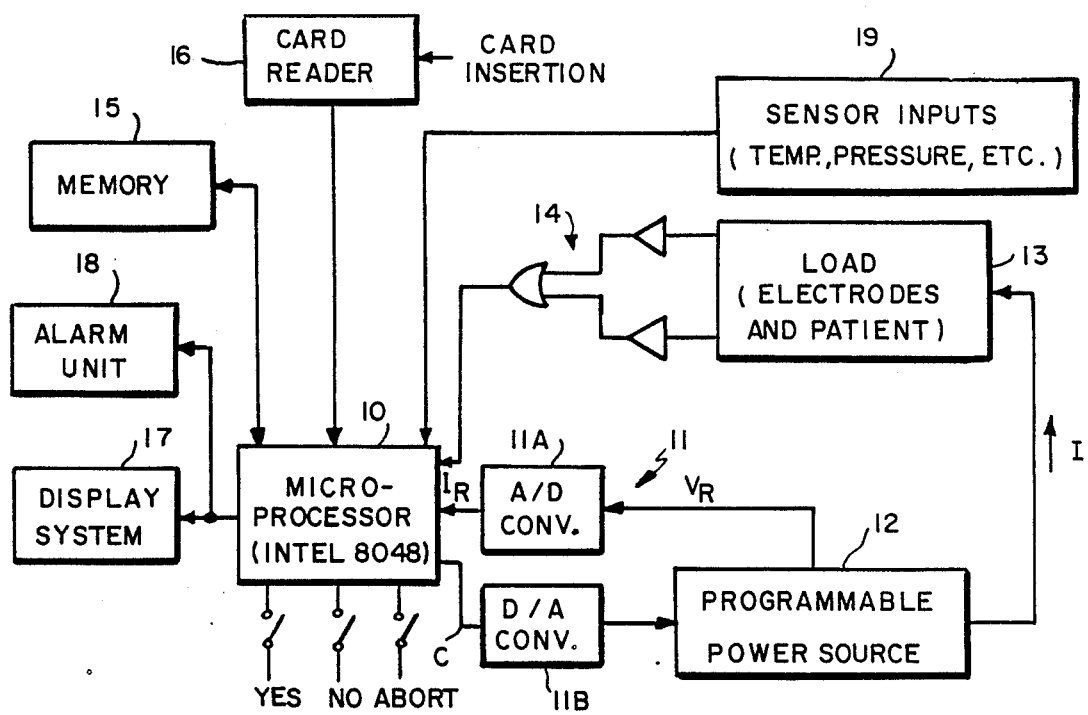
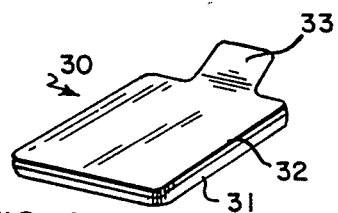
FIG.1
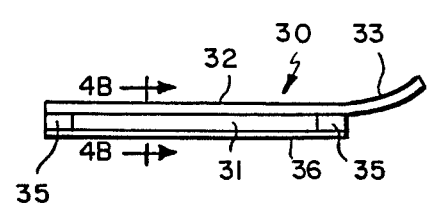
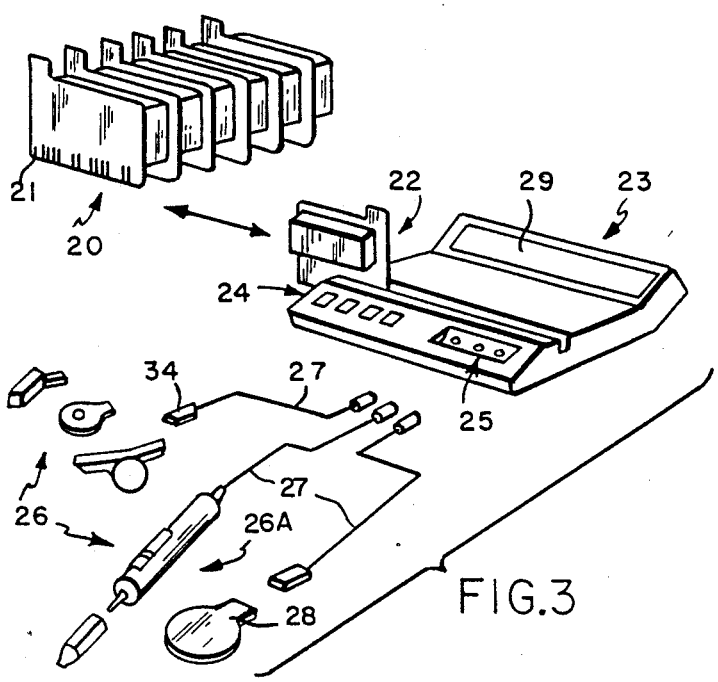
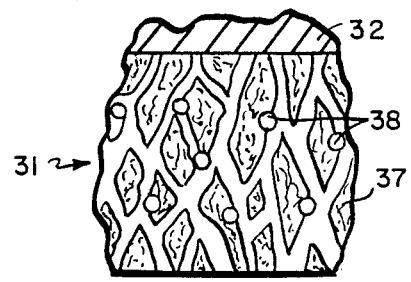

IONTOPHORESIS DRUG DELIVERY SYSTEM

This is a continuation of co-pending application Ser. No. 051,079 filed on May 15, 1987, now abandoned.

INTRODUCTION

This invention relates to drug delivery systems and, more particularly, to systems which deliver medications using iontophoresis techniques.

BACKGROUND OF THE INVENTION

Iontophoresis can by defined a the application of drugs or medications in their ionic forms to the surface of tissues, e.g. to the surface of the skin. An electric current of relatively low amplitude level, as obtained from a voltage having a selected polarity which is opposite to the polarity of charge of the drug ions, is passed through the drug and the body area of the patient into which the drug is to be introduced thereby driving the oppositely charged drug ions transdermally through the skin tissue.

In applying such technique to a patient, an electrode which contains the medication to be introduced is normally positioned over the region of the body which is to be treated and a second electrode, which normally contains a conductive gel, but no medication, is placed at the region of the patient's body opposite thereto so as to form an electric circuit with the current source for the system. Application of a current producing voltage across the electrodes provides desired operating current for causing the ionized molecules of the medication to be transported transdermally into the body portion where the medication can produce its therapeutic effects.

While iontophoresis is a method of administering drugs has been known or many years, little effective use has been made of the technique because the systems purporting to utilize such methods have been too cumbersome, inefficient, and/or costly to find a ready market for them. Moreover, such systems do not permit effective control of the drug delivery rate or provide any effective safety control for the current level which is used. Further, there tends to be a resistance to the use thereof by some patients who may experience traumatic effects from the actual or anticipated use thereof.

It is desirable that an effective system by devised in which the application of the drug dose and the rate at which such dosage is applied can be readily controlled and in which the probability of high patient drug compliance is increased. Such a system should be. one designed so as to provide the desired operation at a reasonable cost and one which can be easily used by a doctor, nurse, or even the patient himself or herself, without fear of harm, of making a mistake, or of causing the system to become inoperative.

BRIEF SUMMARY OF THE INVENTION

A system in accordance with the invention uses a microprocessor having appropriate memory components, a programmable d-c power supply, means for sensing the current level of pulses supplied therefrom, and suitable D/A and A/D interface units for providing a closed loop control system during operation to control the level of the current pulses automatically at a level selected as best for the patient to whom a medication is to be delivered. The system is controlled so that delivery can be terminated prior to completion if the current level exceeds a predetermined maximum allowable level.

The medication is supplied via an electrode in which molecules of the medication in a non-charged state are interspersed throughout a porous or non-porous membrane. Just prior to delivery the membrane is suitably moistened so as to cause such non-charged molecules to be charged.

DESCRIPTION OF THE INVENTION

The invention can be described in more detail with the help of the accompanying drawings wherein FIG. 1 shows a block diagram of a system representing an embodiment of the invention;

FIG. 3 shows a perspective view of an embodiment of the invention; and

Figure 2:
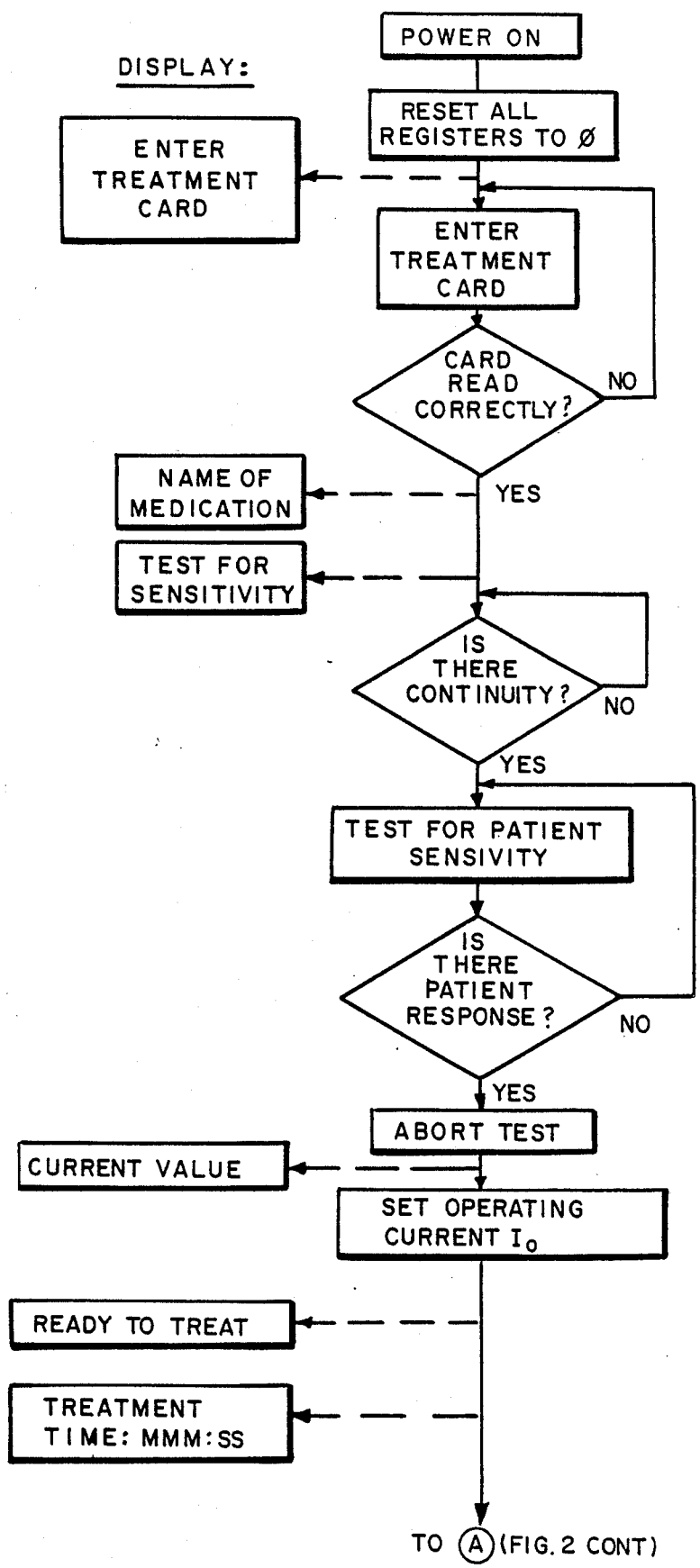
FIG. 2 shows a flow chart depicting the operation of the embodiment of FIG. 1.
Figure 2:
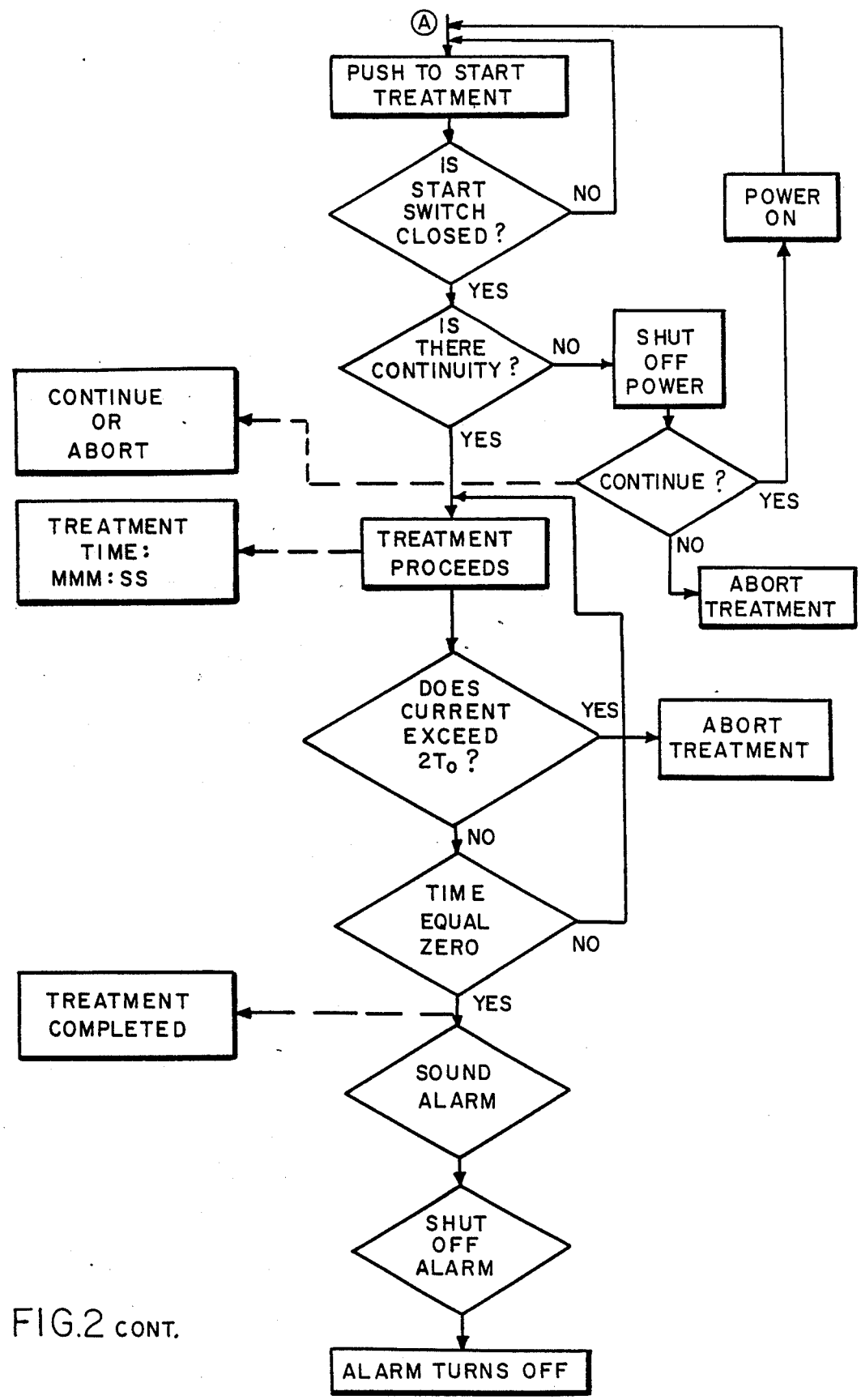

FIG. 4, 4A, AND 4B show various views of a particular embodiment of a medication electrode that can be used in the system of FIGS. 1 and 3.

FIG. 1 shows a block diagram of an embodiment of a system utilizing the techniques of the invention. The system generally comprises three major components, namely, a microprocessor unit 10, an analog/digital interface unit 11, and a programmable power source 12. The power source 12 supplies a voltage across the load 13 so as to produce a current I through the load. The load as shown therein effectively represents the body portion of the patient through which the current flows and the appropriate electrodes, as discussed below, which are attached thereto. The value of the current is monitored by a suitable current sensing, or monitoring, resistor in the power source unit 12, using well known techniques, the value of the monitored current $I_R$ through the resistor being continually supplied to the microprocessor unit 10 through the analog-to-digital (A/D) converter unit 11A of an interface unit 11 for appropriate processing, as discussed below. Digital command signals C are supplied via a digital-to-analog (D/A) converter unit 11B of interface unit 11 to provide analog signal commands for controlling the voltage and, hence, the current output from programmable power source 12.

The microprocessor unit also responds to an appropriate card reader 16 which is used to identify the particular medication which is to be applied to the patient. Card reader 16 supplies, as by means of a bar code on a medication card inserted therein, for example, a coded identification of the medication to the microprocessor unit, as discussed below. A suitable memory system can include ROM and/or RAM memory units, for example, which memory system is used to store predetermined information which is required with respect to a large variety of different medications so that the microprocessor can perform the necessary processing for determining the required treatment times for them. Memory 15 is also used to store one or more application programs which can be appropriately loaded into the microprocessor unit 10 for use thereby. The microprocessor unit 10 further provides appropriate output signals which can be used to control the programmable power source 12, or to display information during treatment, for example, concerning the status of the system on a suitable display system 17. Microprocessor 10 can also supply an output signal for use in actuating a suitable alarm system 18, as discussed below.

The microprocessor unit can be implemented by using any suitably selected microprocessor available to the art, such as the Intel Model 8048 microcomputer available from Intel Corporation of Sunnyvale, Calif., the treatment program micro code being supplied, for example, to the microprocessor as ROM microcode stored in the processor memory system 15.

The programmable power source 12 responds to a command received rom the microprocessor, via D/A converter 11B, for providing voltage output pulses of a desired DC voltage which can be selected within a range from 0 to +150 volts DC, for example, at a selected pulse repetition rate or frequency, e.g. a frequency within a range from about 2 KHz to about 50 KHz, and preferably at 50 KHz to avoid interference with other equipment which may be in the vicinity. A current sensing resistor (not shown) in power source 12 has a known resistance value, the monitored voltage $V_R$ across such known resistance being interpreted by the analog/digital interface unit to produce a digital value $I_R$ representing the current through the load 13.

The microprocessor unit is suitably arranged to fetch the desired treatment program from the memory 15 when treatment is to be initiated. The value of the current during treatment can be displayed on the display unit 17 so that the operator of the device can visually monitor the current level as the system is performing its treatment operation.

In accordance therewith, as described with reference to the flow chart of FIG. 2, when the power is turned on all the registers of the microprocessor are set to zero and the display unit displays the instruction "Enter Treatment Card." The user enters a treatment card into a conventional card reader 16, e.g. one which reads a bar code on the card. When the bar code has been read correctly the microprocessor responds thereto so as to identify the medication to be administered and to display the name of the medication so identified.

Once the medication has been identified the user is instructed to test the patient for sensitivity to the current level which is to be used (at this time the patient has been connected to the system via appropriate electrodes as discussed below). The sensitivity test is performed by a sub-routine program in which pulses of voltage are supplied from programmable power source 12 so as to produce pulses of current through the load 13 which includes the body portion of the patient to which the medication is to be administered and the electrodes at either side thereof. Such current pulses are supplied at a suitably selected frequency e.g. preferably 50 Hz as discussed above. The amplitude level of such current pulses is increased in discrete steps at selected intervals from a relatively low level, e.g. at 0.1 milliamperes (mA.), through incremental steps of 0.1 mA. each until the patient indicates to the operator that he or she begins to feel a perceived sensation, e.g., a tingling type of sensation, at which point the operator can abort the test and note the value of the current at such maximum level which can be referred to as Im. The level of perceived sensation is set automatically as the operating current level, identified as Io, to a value such that the current level which is to by used during treatment to supply the particular medication to the patient is equal to the maximum current value, Im, less a selected fixed current value. Thus, the operating current level for drug delivery is at a value just below the current level at which the patient has first perceived a sensation. For example, in a particular embodiment the constant current level for drug delivery during treatment may be set at a value which is 0.2 mA below the maximum current level which has been indicated by the patient's response (i.e., $Io = Im - 0.2$). The value of the operating current level is then appropriately stored for use by the microprocessor in controlling the dosage for the medication in accordance with the treatment program.

When the operating current level has been set, the microprocessor displays an indication to the user that the system is ready for treatment. Based on the value of the constant operating current level (Im−0.2) mA which has been selected for use and based on the identification of the drug, the microprocessor determines the time of treatment for the particular drug involved, using preset treatment time and current values for each expected medication, which values have been previously stored in the memory 15 associated with the microprocessor.

When the operator pushes a start switch to begin treatment, the microprocessor performs tests to determine if the start switch is closed and to determine if there is electrical continuity through the power source circuitry and the load. If both conditions are satisfied the treatment begins. If continuity is not present the power is shut off and the operator is given the opportunity to check the circuitry and electrical connections involved and to make a determination as to whether treatment should or should not be continued, a sutable display legend (Continue or Abort?) being displayed on display unit 17 for such purpose. If treatment is to continue, the user turns on the power and the above tests are performed again. In accordance therewith the microprocessor then causes the programmable power source to supply pulses of voltage, at the desired 50 KHz frequency, so as to produce current pulses through to the load, the amplitude levels of the current pulses through the load being increased in incremental steps, as before, until the amplitude of the current reaches the operating current level Io. The programmable power source then maintains the voltage at such constant operating current level so as to cause the desired current to be applied through the load to deliver the drug transdermally to the patient.

The monitoring resistor in power source 12 continually monitors the value of the current level and supplies such value to the microprocessor via D/A converter 11A. The overall system thereby forms a closed loop which is used for maintaining the amplitude of the current at the desired level. For example, if such current level exceeds (Im−0.2) mA. the microprocessor commands the programmable power source to reduce the voltage amplitude of the pulses until such current level is reached while, conversely, if the current level drops below (Im−0.2) mA, the microprocessor commands the power source to increase the voltage amplitude until such current level is reached.

As a safety feature, if the monitored current level, for whatever reason, increases to selected value above the desired operating current level, for example, to a value which is twice the operating current level desired, i.e. 2 Io mA. (referred to as the maximum allowable level), the microprocessor automatically shuts off the system so as to avoid any tissue damage or pain which might result from the use of an excessive current through the patient.

So long as the current level is maintained substantially at the desired operating level Io, the medication is delivered to the patient over a time period which is equal to the previously calculated time of treatment. The treatment time is displayed on the display unit, such time display being continually decreased as treatment proceeds so as to inform the user of the time remaining for treatment. Such process can be implemented, for example, by the use of suitable and well known countdown circuitry (not shown) which is activated when the drug delivery operation begins and counts down to zero by the end of the treatment time. When the time left is zero, the display screen indicates that the treatment has been completed and the microprocessor provides a signal to an alarm unit which then appropriately signals that the treatment has been completed, using either a visual and/or an audible alarm device. The user must then shut off the alarm.

The flow chart of such a treatment program as shown in FIG. 2 can be implemented by the microprocessor unit as described above. Using such flow chart, those having skill in the art can readily program any suitable microprocessor main program and any required subroutine programs in order to perform the desired operation of the system as described.

A physical representation of an exemplary system embodying the above described invention is shown in FIG. 3. As can be seen therein, a plurality of medication packages 20 each has imprinted thereon a bar code 21 which identifies the particular medication that is so packaged therein. The portion of the package bearing the bar code can by inserted into an appropriate bar code reader unit 22 within a housing 23 for reading the bar code and supplying the information which has been read to a microprocessing system which is also housed in housing unit and which includes a microprocessor board and an appropriate memory board, or boards, as needed, as well as suitable control switches 24 as required to operate the microprocessing system. Housing 23 also includes appropriate connector terminals 25 for connection via cables 27 to various types of electrodes 26 containing the desired medication, as well as for connection to a suitable ground plane electrode 28. The electrodes are encased in the medication packages 20 so that when the bar code has been read, the electrode containing the desired drug can be removed therefrom and attached via snap clip 34 to one of the cables 27 for use by the system. The drug containing electrode can be of various shapes which can be clipped to a cable connector, as depicted, or it can be a specially designed electrode permanently connected to a cable as shown by electrode 26A, for example.

Housing unit 23 can also include a display unit 29 which may by in the form of a well known liquid crystal display, for example, for displaying alpha-numeric information as supplied to it by the microprocessor. Housing unit 23 also includes the programmable power source 12 (not shown) which supplies the current to the electrodes and the A/D and D/A converter/interface circuitry (not shown) discussed above with reference to FIG. 1. Such components would be well known and readily available to those in the art.

A particular embodiment of a suitable and novel electrode for use in the system of FIGS. 1 and 3 is depicted as electrode 30 shown in FIGS. 4, 4A and 4B. The structure therof comprises a medication layer 31 and an upper conductive foil layer 32 having a contact tab 33 for contacting a snap clip 34 at the end of a cable 27 such as shown in FIG. 3.

A layer 35 of adhesive material is positioned around the periphery of layer 31 as shown in FIG. 4A. A removable strip 36 is placed over the bottom surface of the electrode 30, which layer when removed exposes the lower surfaces of the adhesive layer 35 and the medication layer 31 which are then positioned against the skin of the body location to be treated for adherence thereto. FIG. 4B shows diagramatically a portion of the microstructure of medication layer 31 which comprises a hydrophilic membrane 37 which has interspersed throughout its interior non-ionized molecules 38 of a medication which is to be delivered to the selected body location. Membrane 37 may in some applications be formed as a relatively porous membrane (as shown in FIG. 4B) to assist the migration of the drug molecules therethrough. However, it need not be porous in nature and for some medications such migration will readily occur even if the porosity is relatively low or substantially non-existent. For example, a typical non-porous membrane can be fabricated from a polyurethane material, one such material being made and sold under the model description Ticoflex by Thermedics, Inc. of Woburn, Mass. for retaining a medication such as tetrecyclene, for example. A typical porous membrane can by fabricated from a hydrophilic prepolymer polyurethane, one such material being made and sold under the model designation Hypol 2002 by W. R. Grace Co. of Lexington, Mass. for retaining a medication such as morphine, for example. Such materials are readily available to the art.

Ground electrode 28 in FIG. 3 is of the type, for example, made and sold by Minnesota Mining and Manufacturing Co. of Minneapolis, Minn. under the trade name "Red Devil" and is also adhered to the patients' skin at the surface of the body location opposite to that of the medication electrode by the use of a suitable conductive adhesive normally with the use of a conductive gel, as would be well known in the art.

When the system is ready for delivery of the medication, the exposed lower surface of the electrode is moistened by applying a few drops of water thereto. Since the membrane is hydrophilic, the water is quickly absorbed throughout the membrane and converts the non-ionized molecules of the medication therein to ionized form having a particular predetermined polarity of charge depending on the nature of the medication involved.

The desired current level through the load is produced by power source 12 from a voltage across the load which is selected to have a polarity opposite to that of the polarity of the charged ions of the particular medication being used. Such polarity is determined by the microprocessor using pre-stored information in memory 15 concerning the particular medication in question. The molecular ions migrate through membrane 37 and thence outwardly therefrom into and through the skin of the patient as required.

The system described above can be used for many types of medication treatments and with the help of certain sensed information, as provided by sensor input from a variety of different sensing elements, shown broadly as block 19 in FIG. 1, many advantageous results can be achieved.

For example, in many treatments currently used, a patient is provided with a medication, e.g. a tablet, a capsule, or other form of medication, which must be ingested systemically a selected periodicity e.g. one or more times daily. Such an approach, in order to be effective, normally requires the dosage level to be higher than necessary so as to assure that a sufficient amount of the medication reaches the location at which its therapeutic effect occurs, there being a loss of medication effect as it works its way through the patient's system to the desired location. Moreover, in some cases a patient's need for the medication varies and a more effective use thereof would be to apply the medication only when the patient's metabolic response indicates that medication is required rather than to have the patient take the medication on a constant periodic basis.

For example, patients suffering from hypertension may need medication only when the patient's blood pressure level is above specified limits. It has been found that techniques of photopleythamography using a light emitting diode (LED) element and a light responsive sensor (photodiode) can provide a determination of blood pressure levels. Hence an LED/photodiode sensor system mounted adjacent a patient's skin can provide a sensed output which can be supplied to the microprocessor 10 which in turn can use a known algorithm to compute a sensed blood pressure level. The microprocessor can be arranged to start treatment of a hypertension medication only when the sensed blood pressure level exceeds a known specified limit. Hence, the patient only receives the medication when he or she needs it and receives it transdermally rather than systematically at the desired location. Accordingly, less medication (lower dosages at lower intervals) is used by the patient and side effects of the medication are reduced.

As a further example, diabetic patients who are being treated with insulin may be subject to hypoglycemia shock (due to an excessively low blood sugar level). It is known that if the temperature and electrical conductivity of a patient's skin are determined and if the oxygen content of the patient's blood is determined, a known algorithm can be used to determine the patient's blood sugar content. Such metabolic response can by determined using inputs from appropriate sensors so that microprocessor 10 using such a known algorithm can determine when a patient's blood sugar content drops below a selected level so as to then stop the insulin treatment transdermally. Accordingly, the system of the invention can be used to control the insulin dosage to apply it only when needed, and to do so non-invasively as the patient's metabolic response is continually monitored.

The application of pain killing drugs can also be suitably monitored so as to avoid respiratory failure which may occur if an excessive dosage thereof is given to the patient, thus the patient's heart beat rate can be monitored, as by using well known capacitive sensors for monitoring pulse rates, and supplied to the microprocessor so that if such rate exceeds a selected level during the delivery of a pain killing medication, such delivery can be topped to avoid drug overdose and the possibility of respiratory arrest. Moreover, the microprocessor can also be arranged so that the delivery of a pain killing medication can be activated by the patient himself or herself (as by pushing a start button). The microprocessor can be further programmed so that the patient cannot start a subsequent delivery until a selected time period has elapsed from a previous delivery in order to avoid an excessive dosage. Further, the microprocessor can by programmed so that when a patient is in an extremely painful state, the current level used for delivery can be set to an operating level initially which is much higher than would normally be used (e.g. 2 Io)so that a bolus of the medication can be delivered immediately. The current is then subsequently set at a much lower level than the normal operating level so that the remainder of the medication is delivered at a much lower dosage rate thereafter. Thus, a more immediate therapeutic effect is achieved for a patient in pain distress.

Other programs for monitoring and controlling a dosage delivery rate as well as for triggering or aborting drug delivery can be devised by those in the art using the system and method of the invention for many other applications.

While the particular embodiment of the invention described above represents a preferred embodiment at this time, modifications thereof will occur to those in the art within the spirit and scope of the invention. Hence, the invention is not to be construed as limited to the specific embodiment described, except as defined by the appended clauses.

What is claimed is:

1. A transdermal medication delivery system comprising
   means for retaining a medication in a form such that it is capable of being electrically charged;
   means for identifying the medication in said medication retaining means;
   means for supplying a d-c electrical current through said medication retaining means at a selected body location of a patient to be treated when said medication is in its electrically charged form, said medication retaining means and said body location forming an electrical current path for causing said medication to be delivered from said medication retaining means to said body location transdermally when said electrical current is so supplied;
   current control means for controlling the level of said electrical current in said current path;
   said control means, said medication retaining means, said body location, and said electrical current supplying means forming a closed loop during operation whereby said current is supplied in a controlled manner such that said current is generally maintained at a substantially constant level while said medication is being transdermally delivered to said body location and whereby said delivery can be terminated if said current level exceeds a selected maximum allowable level; and
   said control means further includes time control means responsive to said medication identifying means and to the substantially constant level of said electrical current for determining the treatment time over which said medication is to be delivered and for automatically terminating the delivery of said medication at the expiration of said treatment time.

2. A transdermal medication delivery system in accordance with claim 1 wherein said current supplying means comprises a programmable power source for supplying pulses of a controllable DC voltage having a selected polarity across a load which includes said medication retaining means and said body location so as to produce pulses of said current through said load.

3. A transdermal medication delivery system in accordance with claim 2 wherein said medication retaining means includes
   an electrode for connection to said current supplying means;
   means for retaining molecules of said medication capable of having a charge the polarity of which is opposite to the polarity of said controllable DC voltage.

4. A transdermal medication delivery system in accordance with claim 2 wherein said current supplying means supplies said current in the form of current pulses at a selected pulse repetition rate, or frequency, said current control means controlling the amplitude of said current pulses.

5. A transdermal medication delivery system in accordance with claim 4 wherein said selected pulse repetition rate, or frequency, is within a range from about 2 KHz to about 50 KHz.

6. A transdermal medication delivery system in accordance with claim 1 wherein said control means includes a microprocessor.

7. A transdermal medication delivery system in accordance with claim 1 wherein said medication identifying means includes indication bearing means associated with said medication retaining means for identifying said medication and further wherein said system includes means for reading said indication bearing means to identify said medication and to supply said identification to said control means; and said time control means is responsive to the reading of said identification bearing means and to said substantially constant current level for determining the treatment time over which said medication is to be delivered to said body location and is further responsive to the expiration of said treatment time for terminating the delivery of said medication.

8. A transdermal medication delivery system in accordance with claim 7 wherein said indication bearing means is in the form of a bar code and said reading means is a bar code reader.

9. A transdermal medication delivery system in accordance with claim 1 and further including display means responsive to said control means for displaying selected information related to tho operation of said system.

10. A transdermal medication delivery system in accordance with claim 1 and further including alarm means responsive to said control means for indicating when delivery of said medication to said body location is completed.

11. A transdermal medication delivery system in accordance with claim 1 and further including sensing means for sensing one or more metabolic conditions of said patient, said control means responding to said one or more sensed conditions for further controlling the delivery of said medication to said body location.

12. A transdermal medication delivery system in accordance with claim 11 wherein said control means further controls the delivery of said medication by starting said delivery, by controlling the rate of said delivery, or by stopping said delivery in response to said sensing means.

13. A method of treating a selected body location by introducing a medication transdermally to said body location by applying an electrical current through said medication and said body location, said method comprises the steps of identifying said medication;

determining a selected operating current level;

automatically determining the time of treatment based on the identifying of said medication and on the determining of said selected operating current level;

positioning electrically charged molecules of said medication adjacent to said body location;

applying said electrical current through said medication and said body location, the level of said current being applied in selected incremental steps until said selected operating current level is reached;

maintaining said current at said selected operating current level so as to introduce the charged molecules of said medication into said body location transdermally over said time of treatment; and terminating said treatment when said time of treatment has elapsed.

14. A method in accordance with claim 13 and further including the step of terminating said treatment prior to said elapsed time if the operating current level exceeds a selected maximum allowable value.

15. A method in accordance with claim 14 wherein said selected maximum allowable current level is equal to twice said selected operating current level.

16. A method in accordance with claim 15 wherein said current applying step includes applying said current to said body location and said medication in incremental current amplitude steps until said selected operating current level is reached; and maintaining said selected operating current level substantially constant during said time of treatment.

17. A method in accordance with claim 13 wherein said selected operating current level determining step includes the steps of applying said electrical current to said body location without the presence of said medication in incremental current amplitude steps until a first level of current amplitude is reached at which a patient whose body location is to be medicated feels a perceived sensation; and reducing said current level by a predetermined amount, said operating current level being selected at said reduced current level.

18. A method in accordance with claim 13 wherein said medication positioning step includes selecting a medication package containing non-electrically charged molecules of a medication in a matrix of a hydrophilic membrane;

exposing a portion of said membrane;

moistening the exposed portion of said membrane with water to cause the molecules of medication therein to become electrically charged; and positioning the exposed surface of said membrane with said electrically charged molecules of medication therein adjacent to said body location.

* * * * *